United States Patent
Hagi et al.

(10) Patent No.: US 9,498,127 B2
(45) Date of Patent: Nov. 22, 2016

(54) DATA TRANSFER DEVICE AND DATA TRANSFER SYSTEM

(71) Applicant: TERUMO KABUSHIKI KAISHA, Shibuya-ku (JP)

(72) Inventors: Kouji Hagi, Ashigarakami-gun (JP); Hiromasa Kohno, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 262 days.

(21) Appl. No.: 14/037,623

(22) Filed: Sep. 26, 2013

(65) Prior Publication Data

US 2014/0058222 A1    Feb. 27, 2014

Related U.S. Application Data

(63) Continuation of application No. PCT/JP2011/006948, filed on Dec. 13, 2011.

(30) Foreign Application Priority Data

Mar. 29, 2011    (JP) ................. 2011-071315

(51) Int. Cl.
*A61B 5/00*      (2006.01)
*A61B 5/145*    (2006.01)
(Continued)

(52) U.S. Cl.
CPC ........... *A61B 5/0002* (2013.01); *A61B 5/1459* (2013.01); *A61B 5/1495* (2013.01);
(Continued)

(58) Field of Classification Search
CPC .............. A61B 5/145; A61B 5/14532; A61B 5/14535; A61B 5/14539; A61B 5/1455; A61B 5/14556; A61B 5/1486; A61M 5/1723; A61M 2005/1726; A61M 2230/20; A61M 2230/201

USPC ....... 600/300, 309, 316, 317, 322–329, 365; 604/4.01, 6.08, 504; 128/898
See application file for complete search history.

(56) References Cited

U.S. PATENT DOCUMENTS 6,572,542 B1 * 6/2003 Houben ............... A61B 5/0472
                                                          128/920
6,809,653 B1   10/2004 Mann et al.
(Continued)

FOREIGN PATENT DOCUMENTS

| JP | 2002-526137 A | 8/2002 |
| JP | 2008-246204 A | 10/2008 |
| JP | 2009-229269 A | 10/2009 |

OTHER PUBLICATIONS

Medtrnic Diabetes "Innovation Milestones."*
(Continued)

*Primary Examiner* — Ahmed Farah
(74) *Attorney, Agent, or Firm* — Buchanan Ingersoll & Rooney PC

(57) ABSTRACT

A device for receiving a transmitting unit that is detachably attachable to a sensor unit configured to be placed on a subject to acquire a biosignal of the subject and that acquires bio-information from the biosignal acquired in the sensor unit to transmit the biosignal to an external device. This device has first and second ports on which transmitting units can be placed, and communication sections each provided in a respective one of the ports to carry out communication with the transmitting units mounted on the respective ports. When the transmitting unit is newly mounted on one port, the device acquires transmission data including communication identification information for the transmission from the newly mounted transmitting unit by the communication section of this port and transmits the acquired transmission data to another transmitting unit already mounted on the other port by using the communication section provided in the other port.

17 Claims, 9 Drawing Sheets

(51) Int. Cl.
    *A61B 5/1459*     (2006.01)
    *A61B 5/1495*     (2006.01)
    *A61B 10/00*     (2006.01)

(52) U.S. Cl.
    CPC ....... *A61B5/14503* (2013.01); *A61B 5/14514* (2013.01); *A61B 5/14532* (2013.01); *A61B 5/14546* (2013.01); *A61B 5/6833* (2013.01); *A61B 5/6848* (2013.01); *A61B 5/742* (2013.01); *A61B 10/0045* (2013.01); *A61B 5/6832* (2013.01); *A61B 2560/0219* (2013.01); *A61B 2560/0412* (2013.01)

(56) References Cited

U.S. PATENT DOCUMENTS

| | | | | |
|---|---|---|---|---|
| 7,044,911 B2* | 5/2006 | Drinan | ............... | A61B 5/14539 128/903 |
| 7,468,033 B2* | 12/2008 | Van Antwerp | ....... | A61B 5/0002 600/300 |
| 8,145,267 B2* | 3/2012 | Okuda | ................ | A61B 5/0002 455/154.1 |
| 8,597,570 B2* | 12/2013 | Terashima | ........... | A61B 5/4839 422/68.1 |
| 8,622,901 B2* | 1/2014 | Jain | ..................... | A61B 5/0022 600/300 |
| 2006/0052745 A1* | 3/2006 | Van Antwerp | ....... | A61B 5/0002 604/67 |
| 2008/0242962 A1 | 10/2008 | Roesicke et al. | | |
| 2009/0240120 A1* | 9/2009 | Mensinger | ........... | A61B 5/7445 600/301 |
| 2010/0159835 A1* | 6/2010 | Aoki | .................... | A61B 5/0002 455/41.3 |
| 2010/0262117 A1* | 10/2010 | Magni | ................. | A61B 5/14532 604/504 |
| 2011/0015502 A1* | 1/2011 | Peyser | ............... | A61B 5/14532 600/301 |
| 2011/0160555 A1* | 6/2011 | Reifman | ............ | A61B 5/14532 600/365 |
| 2012/0323101 A1* | 12/2012 | Kohno | ................. | A61B 5/1459 600/365 |
| 2014/0012116 A1* | 1/2014 | Okuyama | ............ | A61B 5/7445 600/347 |
| 2014/0024908 A1* | 1/2014 | Hagi | .................. | A61B 5/14532 600/365 |

OTHER PUBLICATIONS

Miniged 530G Insulin Pump.*
International Search Report (PCT/ISA/210) mailed on Feb. 28, 2012, by the Japanese Patent Office as the International Searching Authority for International Application No. PCT/JP2011/006948.

* cited by examiner

F I G . 3
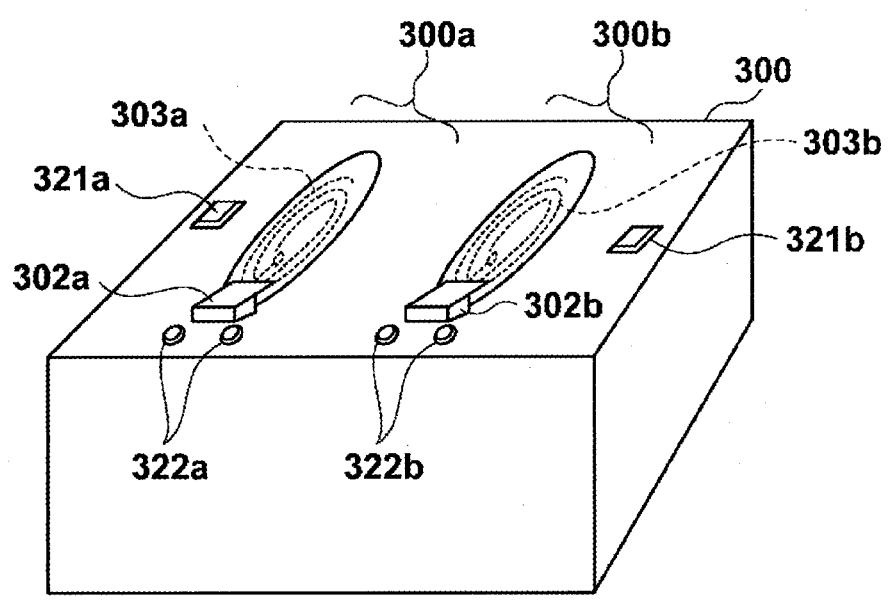

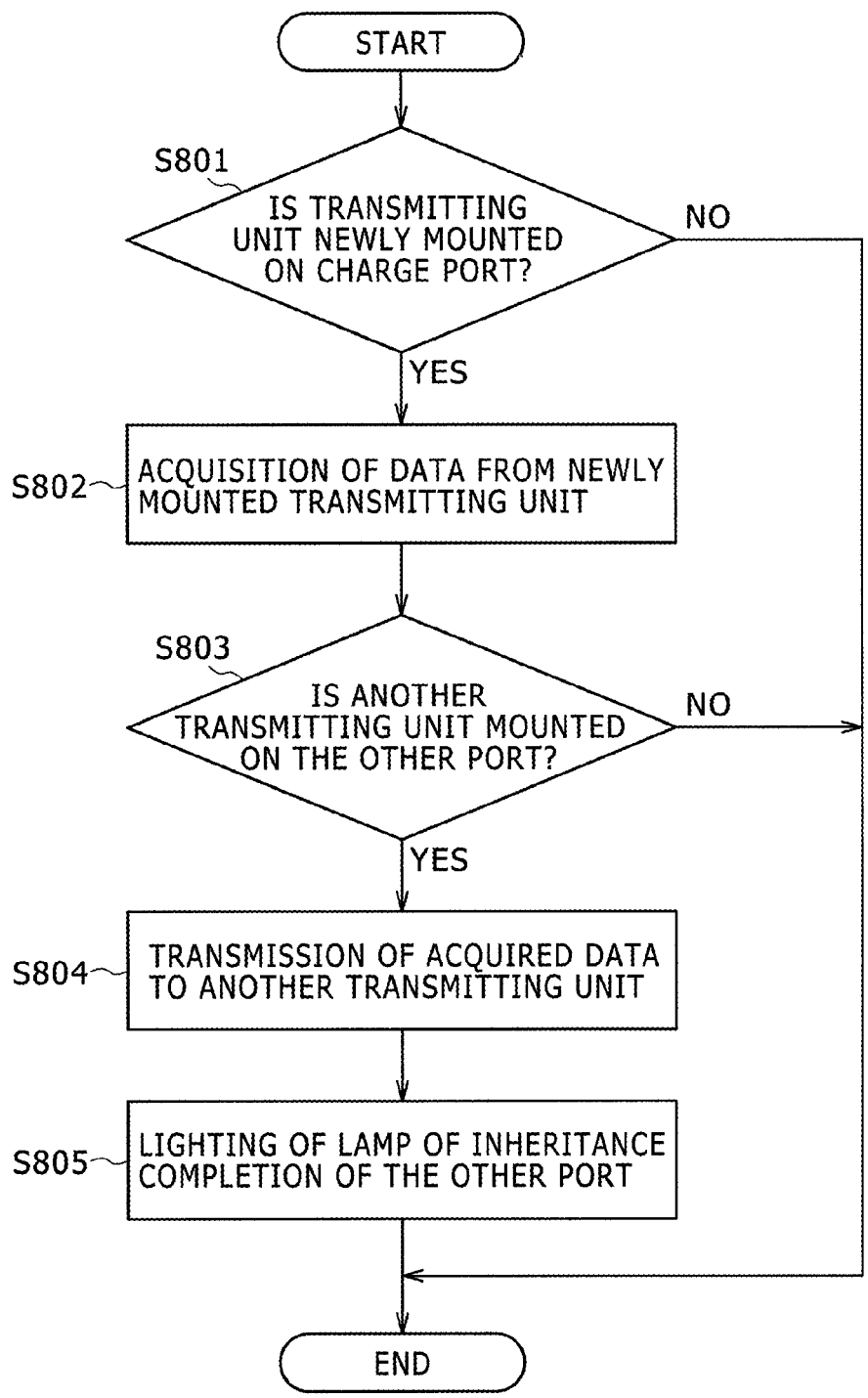

DATA TRANSFER DEVICE AND DATA TRANSFER SYSTEM

CROSS REFERENCES TO RELATED APPLICATIONS

This application claims is a continuation of International Application No. PCT/JP2011/006948 filed on Dec. 13, 2011, and claims priority to Japanese Application No. 2011-071315 filed on Mar. 29, 2011, the entire content of both of which is incorporated herein by reference.

TECHNICAL FIELD

The present invention generally relates to a data transfer device, a data transfer system and a data transfer method suitable for a bio-information measuring system to measure bio-information of a subject intermittently or continuously.

BACKGROUND DISCUSSION

As a bio-information measuring system to measure bio-information of a subject intermittently or continuously, a body fluid component measuring system that measures body fluid of the subject intermittently or continuously and displays a blood glucose level is known. Conventionally, so-called self-monitoring of blood glucose (SMBG), in which blood drawn by puncturing a fingertip or the like by a dedicated puncture device is measured by a blood glucose meter each time blood is drawn, has been widely used as a method for a diabetic to measure and manage the blood glucose level for himself/herself.

As an alternative, a body fluid component measuring system allowing continuous glucose monitoring (CGM), in which the blood glucose level of a subject is continuously monitored with a sensor positioned indwelling in a skin by making a puncture under the skin or the like with a needle disposed on a dedicated sensor unit, has recently been developed (see Japanese Application Publication No. 2002-526137, for example), and has already been put to practical use in Europe and America.

The body fluid component measuring system used for the CGM is composed of the sensor unit always mounted on a subject, a transmitting unit that is attached to this sensor unit and transmits a measurement signal in this sensor unit to the external, and a display device that calculates a blood glucose level based on the measurement signal transmitted from this transmitting unit and displays this blood glucose level. This system is such that the sensor unit is replaced with a new sensor unit at a frequency of about once every three days to one week.

The transmitting unit and the display device, on the other hand, are continuously used irrespective of the replacement of the sensor unit, and use over a long period is allowed by repeatedly carrying out charging or replacement of a battery.

However, it is undesirable that the monitoring of the blood glucose level of a subject is interrupted for a long time every time the battery mounted in the transmitting unit and the display device needs to be charged or replaced. On the other hand, it becomes possible to reduce the cumulative total value of the time for which the monitoring of the blood glucose level is interrupted by decreasing the charging frequency or replacement frequency of the battery mounted in the transmitting unit and the display device. However, in this case, the size of the battery mounted in the transmitting unit and the display device becomes large and therefore convenience decreases for the subject on which they are always mounted.

For such circumstances, in the body fluid component measuring system that measures body fluid of a subject intermittently or continuously and displays the concentration of a predetermined body fluid component, it is desirable to allow shortening of the time for which monitoring of the concentration of this body fluid component is interrupted without impairing convenience for the subject.

SUMMARY

According to one aspect, a data transfer device receives respective transmitting units that are individually detachably attachable to a sensor unit configured to be at least partially placed in a living body of a subject to acquire a biosignal of the subject and to acquire bio-information from the biosignal acquired in the sensor unit to transmit the bio-information to an external unit. The data transfer device comprises: a first port on which a first transmitting unit is to be placed and a second port on which a second transmitting unit is to be placed; a first communication section provided at the first port and communicating with the first transmitting unit when the first transmitting unit is mounted on the first port, and a second communication section provided at the second port and communicating with the second transmitting unit when the second transmitting unit is mounted on the second port; data acquiring means for acquiring transmission data, including communication identification information for transmitting the bio-information from one of the first and second transmitting units to the external unit, by the communication section provided in one of the first port and the second port when the respective first transmitting unit and the second transmitting unit is newly placed on the one of the first port and the second port; and transmitting means that transmits the transmission data acquired by the data acquiring means to the other of the first and second transmitting units by using the communication section provided in the other port when the other of the first and second transmitting units is already mounted on the other of the first and second ports.

Information of the transmitting unit before replacement is inherited or transferred to the replacing transmitting unit. Therefore, it is possible to provide a configuration capable of shortening the time for which monitoring of predetermined bio-information is interrupted without impairing convenience for the subject.

According to another aspect, a data transfer system comprises: at least two transmitting units each separately detachably attachable to a sensor unit which is configured to be at least partially placed in a living body of a subject to acquire a biosignal of the subject, one of the transmitting units being configured to acquire bio-information from the biosignal acquired in the sensor unit to transmit the bio-information, wherein the at least two transmitting units comprise one transmitting unit and an other transmitting unit; an external unit that receives the bio-information transmitted from one of the transmitting units; and a data transfer device. The data transfer device comprises: first and second ports at which respective ones of the transmitting units are to be individually placed; a first communication section provided at the first port and communicating with one of the transmitting units placed at the first port, and a second communication section provided at the second port and communicating with an other of the transmitting units placed at the second port; data acquiring means for acquiring transmission data including communication identification information for transmitting to the external device the bio-information from the transmitting unit placed at either one of the first and second ports when the transmitting unit is newly placed at the one port; and transmitting means for transmitting the transmission data acquired by the data acquiring means to the transmitting unit placed at the other of the first and second ports by using the communication section provided in the other of the first and second ports when another of the transmitting units is placed at the other of the first and second ports.

Another aspect involves a method of transferring data from one transmitting unit placed at a first port of a transfer device, the one transmitting unit being detachably attachable to a sensor unit configured to be at least partially placed in a living body of a subject to acquire a biosignal of the subject, and the one transmitting unit acquiring bio-information based on the biosignal acquired in the sensor unit to transmit the bio-information to an external unit, the transfer device including a second port different from the first port. The method comprises: determining that an other transmitting unit different from the one transmitting unit is newly placed at the second port of the transfer device, wherein the other transmitting unit possesses transmission data including communication identification information for transmitting the bio-information; the transfer device acquiring the transmission data, including the communication identification information for transmitting the bio-information, from the other transmitting unit; and the transfer device transmitting, to the one transmitting unit placed at the first port of the transfer device, the transmission data, including the communication identification information for transmitting the bio-information, acquired from the other transmitting unit.

Other aspects and characteristics of the data transfer device, data transfer system and data transfer method will become apparent by the following detailed description considered with reference to the accompanying drawings in which like elements are designated by like reference numerals.

BRIEF DESCRIPTION OF DRAWINGS

The accompanying drawings are included in the specification, constitute a part of the specification, and are used for showing embodiments of the device and system disclosed here while also explaining principles of the disclosed device and system.

FIG. 3 is a perspective view of a charge device.

FIG. 9 is a flowchart explaining operation of the charge device.

DETAILED DESCRIPTION

Embodiments of the data transfer device and a data transfer system will be described below with reference to the accompanying drawings. The following, description will consider an example in which the data transfer device and a data transfer system are applied to or used in connection with a body fluid component measuring system that treats measurement data obtained by measuring a body fluid component as a biosignal and acquires a blood glucose level as bio-information from this biosignal. However, the biosignal and the bio-information as the object are not limited in this regard.

1. Appearance Configuration of Body Fluid Component Measuring System

Figure 1:
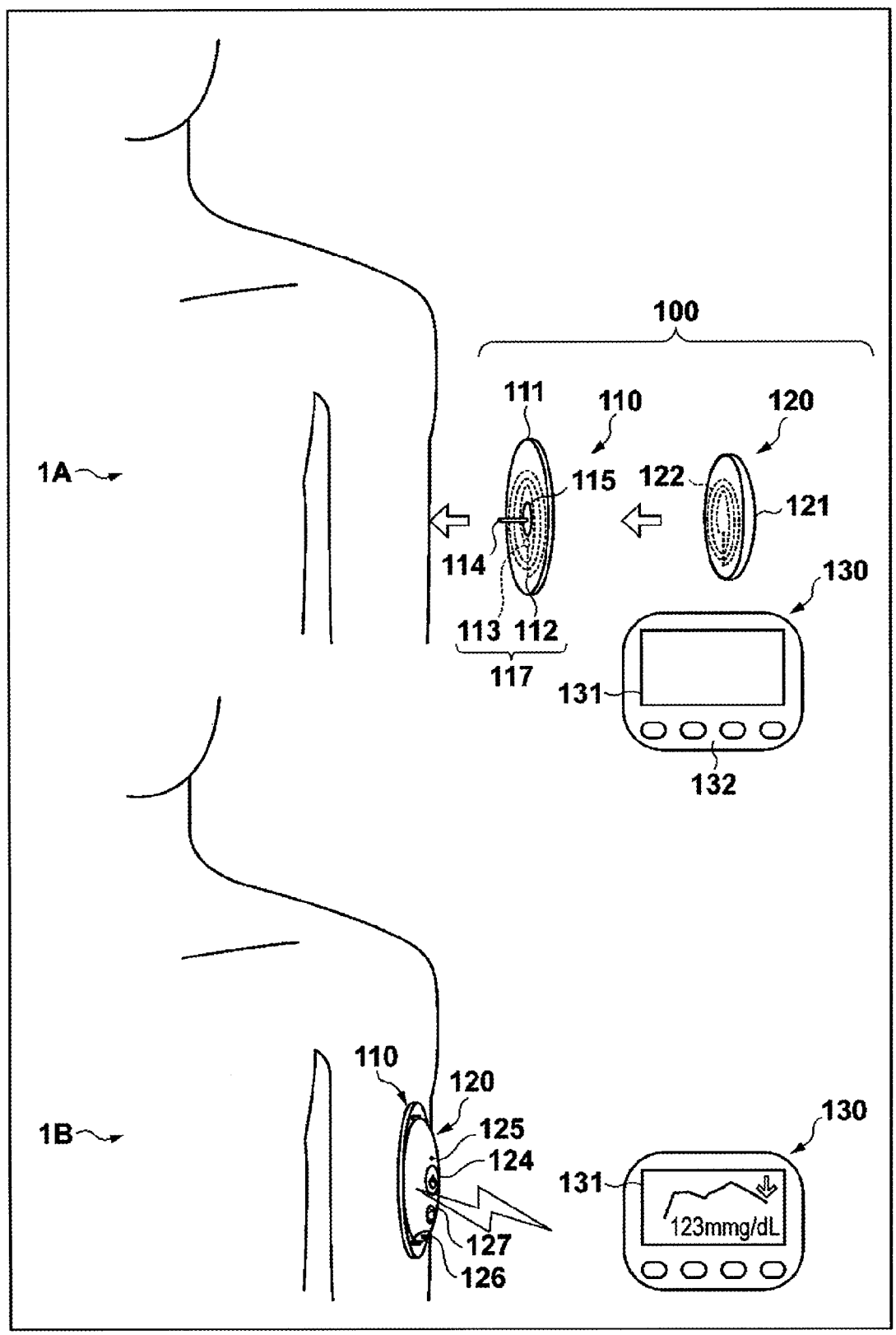
FIG. 1 is a schematic illustration showing an external constitution of a body fluid component measuring system according to one embodiment disclosed here.

FIG. 1 illustrates the external constitution of a body fluid component measuring system 100 according to one embodiment disclosed here. As shown in 1A of FIG. 1, the body fluid component measuring system 100 includes a sensor unit 110, a transmitting unit 120, and a display unit 130.

The sensor unit 110 includes a main body portion 111 constructed in a liquid-tight manner or structure of hard plastic, metal, ceramic, or the like that can prevent liquids from infiltrating or penetrating. Examples of the hard plastic include an ABS resin, polypropylene, polycarbonate, and a flexible resin such as polyurethane or the like. Examples of the metal include SUS and titanium. Examples of the ceramic include zirconia and the like. A skin sticking tape (adhesive tape) having a waterproof function is disposed on the bottom surface of the main body portion 111. Therefore the sensor unit 110 can be stuck or adhered directly to an upper arm region, an abdominal region, or the like of a subject and held at such position by the adhesive.

Further, a needle 114 to be positioned indwelling in the skin of the subject and to come into contact with a body fluid under the skin is provided on, and projects from, the bottom surface of the main body portion 111, and is connected to a component measuring section 115 disposed within the main body portion 111. The component measuring section 115 outputs a measurement signal corresponding to the quantity of a predetermined body fluid component such as glucose, lactic acid, or the like in an interstitial fluid as the body fluid under the skin with which body fluid the needle 114 comes into contact.

An IC tag 117 with a built-in A/D circuit (hereinafter referred to simply as an IC tag 117), which IC tag includes an antenna 112 and an IC (integrated circuit) chip 113 is provided inside the main body portion 111. The IC tag 117 operates by using, as a power supply, an electromotive force arising due to an electromagnetic field generated in the transmitting unit 120. The IC tag 117 controls measurement by the component measuring section 115 and transmits measurement data, obtained as the result of the measurement, to the transmitting unit 120.

The transmitting unit 120 includes a housing 121. Inside the housing 121, an IC tag transmitting/receiving module 122 for contactless access to the IC tag 117 is disposed. The IC tag transmitting/receiving module 122 is driven to generate an electromagnetic field for the IC tag 117 of the sensor unit 110 and supply power by electromagnetic induction. In addition, the IC tag transmitting/receiving module 122 receives the measurement data indicating the measurement result by detecting change in an electromagnetic field generated in the IC tag 117. The transmitting unit 120 processes the measurement data received from the sensor unit 110 to calculate the concentration of a predetermined body fluid component contained in body fluid, such as glucose (concentration of a predetermined body fluid component in body fluid as a component that is allogeneic or xenogeneic to the body fluid) and stores the obtained concentration in a memory. Details of the configuration of the IC tag transmitting/receiving module 122 will be described later with reference to FIG. 2.

Furthermore, a locking part is provided at the bottom surface of the housing 121 and the back surface of the main body part 111, which allows the transmitting unit 120 to be attached/detached to/from the sensor unit 110. That is, the transmitting unit 120 is removably or detachably attached to the sensor unit 110.

The display unit 130 has a display area 131 and displays the concentration of the body fluid component, read out from the sensor unit 110 and transmitted to the display unit 130 by the transmitting unit 120, based on a user order from an input section 132. Furthermore, the display unit 130 has the input section 132 and accepts various kinds of operation, such as changeover of displayed content on the display area 131 and input of predetermined information.

1B of FIG. 1 is a diagram showing the state in which the transmitting unit 120 is attached to the sensor unit 110. As shown in 1B of FIG. 1, a power switch 124 for turning on/off the power supply of the transmitting unit 120 is provided on the back surface of the transmitting unit 120. By pressing the power switch 124 once, the power supply is turned on and a lamp 125 is lighted. Furthermore, by pressing it one more time, the power supply is turned off and the lamp 125 is turned off.

Moreover, a speaker 127 is provided on the back surface of the transmitting unit 120 and outputs a sound (audible notifications) to the subject e.g. when an error or the like is detected in the transmitting unit 120. Furthermore, a charge connector 126 is provided on the back surface of the transmitting unit 120. It is connected (connectable) to a charge device to be described later, which can charge a secondary battery (chargeable battery) incorporated in the transmitting unit 120.

Based on the above-described configuration, when the power switch 124 is pressed to turn on the power supply of the transmitting unit 120 in the state in which the transmitting unit 120 is attached to the sensor unit 110, measurement data is wirelessly transmitted from the transmitting unit 120 to the display unit 130. The display unit 130 accumulates the transmitted measurement data and allows viewing of the concentration of the predetermined body fluid component at every predetermined cycle. The display unit 130 shown in 1B of FIG. 1 is one to show the state in which the concentration of the body fluid component obtained by present measurement is displayed with a trend graph on the display area 131.

2. Functional Configuration of Body Fluid Component Measuring System

Figure 2:
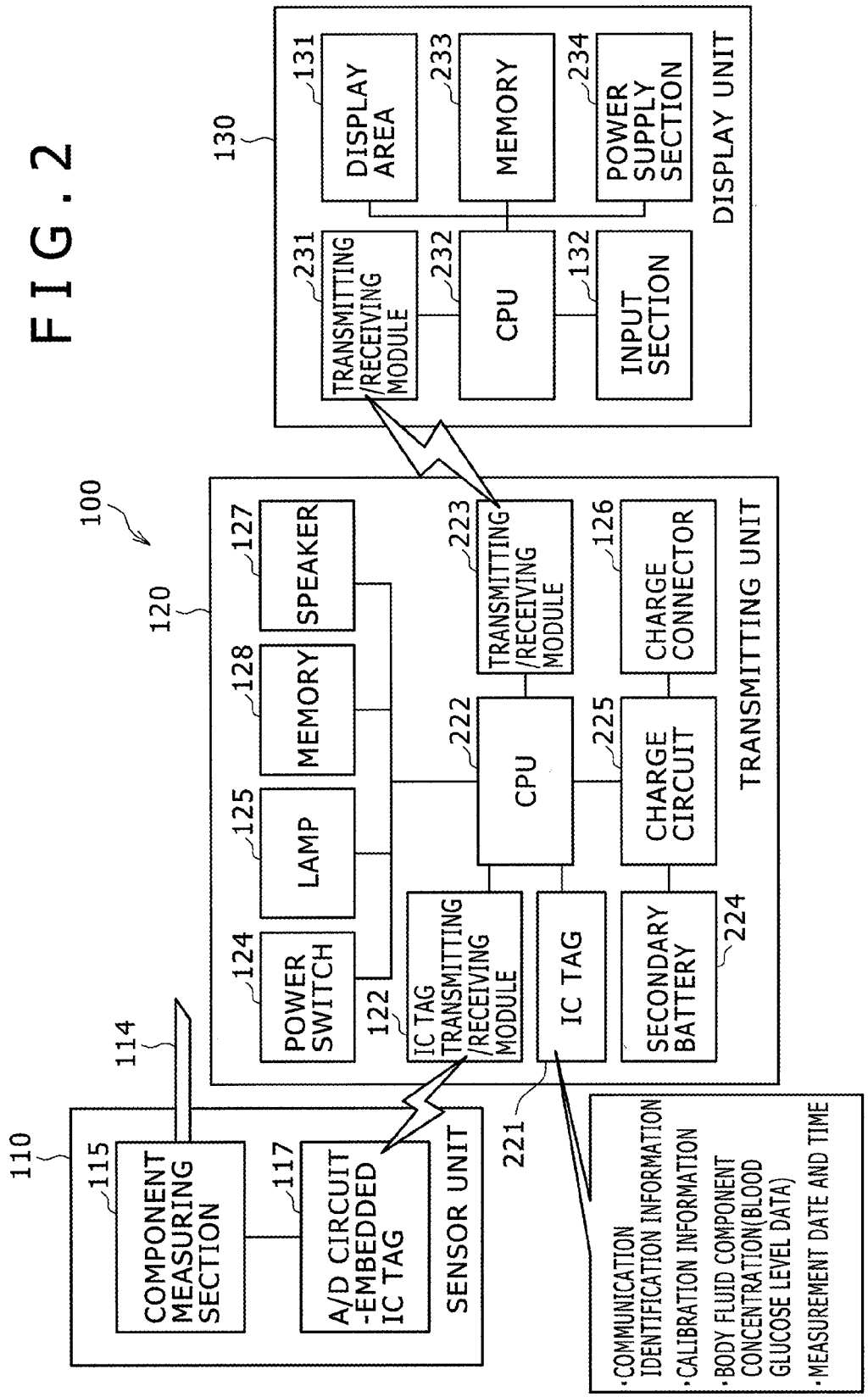
FIG. 2 is a diagram showing the functional configuration of the body fluid component measuring system 100.

Next, the functional configuration of the body fluid component measuring system 100 will be described. FIG. 2 is a diagram showing the functional configuration of the body fluid component measuring system 100. In FIG. 2, elements or features corresponding to elements or features that have already been described above are identified by a common reference numeral.

As shown in FIG. 2, the sensor unit 110 includes the needle 114, the component measuring section 115, and the IC tag 117. The needle 114 is a capillary tube that induces body fluid flow so that the body fluid is able to reach the component measuring section 115 and is set to such a length that its tip reaches subcutaneous tissue of a subject. The needle 114 is connected to the component measuring section 115 and induces body fluid into the component measuring section 115. Furthermore, it is also possible to employ a configuration in which the component measuring section is disposed near the tip part of the needle 114 and component measurement of body fluid in subcutaneous tissue of a subject is performed.

The component measuring section 115 is measuring means for measuring the concentration of a predetermined body fluid component contained in body fluid (e.g. glucose, uric acid, cholesterol, protein, mineral, blood cell, etc.) and carries out measurement by using a well-known measuring method. As the body fluid conducted by the needle 114, blood, interstitial fluid, lymph, etc. are cited. Furthermore, for the measurement of the body fluid component, a method of measuring fluorescence intensity when a fluorescent dye to capture the predetermined body fluid component contained in the body fluid as the measurement target is irradiated with excitation light, a method of optically or electrochemically measuring the predetermined body fluid component contained in the body fluid as the measurement target by using an oxidase, or the like is used.

In the body fluid component measuring system according to the present embodiment, the needle 114 is placed beneath the skin and the glucose concentration in interstitial fluid is measured to convert it to the glucose concentration in blood (blood glucose level). Furthermore, as the measuring sensor, a fluorescent sensor in which a boronic acid group-introduced fluorescent dye linked to sugars to show a Stokes shift is fixed to a hydrogel, a GOD sensor that utilizes a glucose oxidase (GOD) and uses a redox electrode obtained by fixing the GOD to an electrode or the like, etc. is used. It is also possible to employ a configuration in which, instead of positioning the needle tip in subcutaneous tissue, a blood vessel is punctured by the needle 114 to directly measure the glucose concentration in blood.

The IC tag 117 controls the component measuring section 115 by an electromotive force arising due to an electromagnetic field generated in the IC tag transmitting/receiving module 122 of the transmitting unit 120. Furthermore, IC tag 117 transmits, to the transmitting unit 120, digital measurement data obtained by performing A/D conversion of a measurement result from the component measuring section 115.

The transmitting unit 120 includes the power switch 124, the lamp 125, a memory 128, the speaker 127, the IC tag transmitting/receiving module 122, an IC tag 221, a central arithmetic processing device (central processing unit: CPU) 222, a transmitting/receiving module 223, a secondary battery 224, a charge circuit 225, and the charge connector 126. The CPU 222 includes a ROM to store a control program run by the CPU 222 and various kinds of data, a RAM to primarily store various kinds of data as a work area, and so forth, and serves as a control section that executes processing and determination in the respective steps.

By pressing the power switch 124, the power supply of the transmitting unit 120 is turned on and the lamp 125 is lighted. The lamp 125 may be configured to blink when the remaining level of the secondary battery 224 has become low to thereby notify the user that the remaining level of the secondary battery 224 is low. Furthermore, the lamp 125 may be configured light with different colors depending on the internal state of the transmitting unit 120 (for example it may be configured to light with green in the normal case and to light with red when an unusual case is detected).

In the memory 128, the following programs are stored: a calculation program to calculate the concentration of the predetermined body fluid component contained in body fluid based on digital measurement data, which is a measurement result received from the sensor unit 110, and calibration information; a calibration program for calculating the calibration information used in the calculation of the concentration of the body fluid component; a control program to control the operation of the whole of the transmitting unit 120; etc. The calculation program is prepared for different body fluids as the measurement target and for different body fluid components as the calculation target. This allows the transmitting unit 120 to calculate the concentration of a variety of body fluid components. Examples of body fluids as a measurement object include blood, interstitial fluid, lymph, or the like. Examples of the body fluid component as a calculation object include glucose, uric acid, cholesterol, protein, a mineral, blood cells, or the like.

The speaker 127 informs the measurement end, the concentration of the measured body fluid component, and so forth by a sound. For example, the speaker outputs a short beep sound when a blood glucose level obtained as the result of measurement is normal and continuously outputs a warning sound larger (e.g., louder) than the sound of the normal case when the blood glucose level is unusual.

The IC tag transmitting/receiving module 122 supplies power to the sensor unit 110 and performs transmission and reception of various kinds of information between the transmitting unit 120 and the sensor unit 110. The CPU 222 controls the operation of the whole of the transmitting unit 120, including processing to be described later with reference to FIGS. 6 to 8. The transmitting/receiving module 223 is a communication module for wirelessly transmitting, to the display unit 130, the concentration of the body fluid component and the corresponding measurement date and time read out from the sensor unit 110 by using the IC tag transmitting/receiving module 122 based on an order from the display unit 130.

Figure 4:
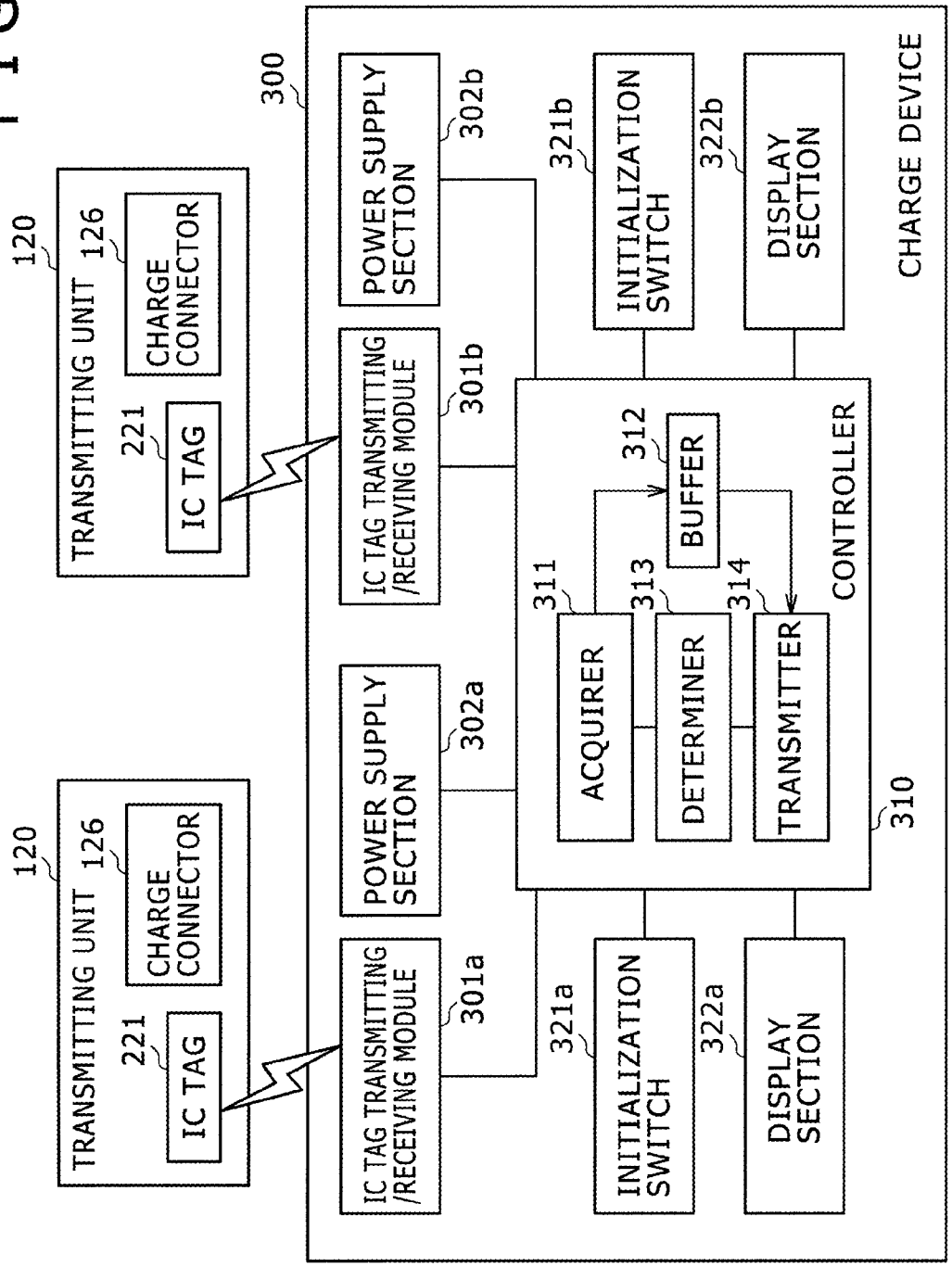
FIG. 4 is a block diagram explaining the configuration of the charge device.

Furthermore, the IC tag 221 stores data read by IC tag reader/writers (IC tag transmitting/receiving modules 301*a* and 301*b* in FIG. 4) included in a charge device 300 shown in FIGS. 3 and 4. Due to this configuration, the charge device 300 can acquire data from the IC tag 221 even when the power switch 124 of the transmitting unit 120 is in the off-state or the transmitting unit 120 is being charged. Data writing to the IC tag 221 can be performed from both the CPU 222 and the charge device 300 (IC tag transmitting/receiving modules). In a memory of an IC chip configuring the IC tag 221, e.g. the following data are stored.

communication identification information used in wireless communication between the transmitting/receiving module 223 of the transmitting unit 120 and a transmitting/receiving module 231 of the display unit 130, the concentration of a body fluid component, such as a blood glucose level, calculated in the transmitting unit 120 based on measurement data transmitted from the sensor unit 110 to the transmitting unit 120, measurement date and time of the above-described concentration of a body fluid component, and calibration information used in the calculation of the concentration of a body fluid component, such as a blood glucose level, in the transmitting unit 120.

The measurement date and time are stored in association with the corresponding concentration of the body fluid component. This allows the display unit 130 to acquire the concentration of the measured component and the measurement date and time thereof and perform trend display and so forth without receiving a measurement result in real time.

The secondary battery 224 supplies power to the respective sections configuring the transmitting unit 120. The charge circuit 225 is a circuit for charging the secondary battery 224 and charges the secondary battery 224 when supplied with power from the charge device 300 via the charge connector 126.

The display unit 130 includes the transmitting/receiving module 231, a CPU 232, the input section 132, the display area 131, a memory 233, and a power supply section 234. The CPU 232 includes a ROM to store a control program run by the CPU 232 and various kinds of data, a RAM to primarily store various kinds of data as a work area, and so forth, and serves as a control section that executes processing and determination in the respective steps.

The transmitting/receiving module 231 receives the concentration of the body fluid component and measurement date and time transmitted from the transmitting unit 120 via the transmitting/receiving module 223. The concentration of the body fluid component received in the transmitting/receiving module 231 is processed in the CPU 232 to be displayed on the display area 131 and stored in the memory 233. In order to make the time of a clock possessed by the display unit 130 correspond with the time of a clock possessed by the transmitting unit 120, time information may be exchanged.

The input section 132 is a button, for example, to accept an input order of a subject. It is used for operations such as an order of powering-on to the display unit 130, an order of calling to the transmitting unit 120 about a previously calculated concentration of a body fluid component, an order of changeover of display, and information input for calculating the calibration information used in calculation of the concentration of a body fluid component. The display area 131 and the input section 132 may be formed by one part such as a touch panel. The power supply section 234 is a battery to supply power to the respective sections configuring the display unit 130.

3. Functional Configuration of Charge Device

Next, the charge device 300 for charging the transmitting unit 120 will be described. FIG. 3 is a diagram showing one example of the charge device 300, and FIG. 4 is a block diagram showing a configuration example of the charge device 300. The charge device 300 of the present embodiment has a first charge port 300*a* as a first port on which the transmitting unit 120 is mounted to charge the transmitting unit 120 and a second charge port 300*b* as a second port. The ports 30*a*, 300*b* can be openings or apertures into which the transmitting units are inserted or can be areas to position the transmitting units. The respective charge ports have power supply connectors 302*a* and 302*b* for connecting to the charge connector 126 of the transmitting unit 120 to supply charge power. In FIG. 3, the power supply connector provided in the first charge port is identified by reference symbol 302*a* and the power supply connector provided in the second charge port is identified by reference symbol 302*b*. Furthermore, in each charge port, an antenna of the IC tag transmitting/receiving module functioning as a reader/writer of the IC tag 221 of the transmitting unit 120 is provided. That is, the IC tag transmitting/receiving module 301*a* and an antenna 303*a* are used for communication with the transmitting unit 120 mounted on the first charge port, and the IC tag transmitting/receiving module 301*b* and an antenna 303*b* are used for communication with the transmitting unit 120 mounted on the second charge port. In FIG. 3, lamps 322*a* and 322*b* notify the user of charge completion and data inheritance completion by control of a controller 310. Furthermore, an initialization switch 321a is a switch for resetting and initializing the IC tag 221 of the transmitting unit 120 mounted on the first charge port 300a. Similarly, an initialization switch 321b is a switch for resetting and initializing the IC tag 221 of the transmitting unit 120 mounted on the second charge port 300b.

Furthermore, in the charge device 300, the controller 310 controls data transfer between two transmitting units 120 mounted on the first and second charge ports (300a and 300b) of the charge device 300 by using the IC tag transmitting/receiving modules 301a and 301b. The IC tag transmitting/receiving module 301a is an example of a first communication section provided at the first port and communicating with the first transmitting unit when the first transmitting unit is mounted on the first port, and the IC tag transmitting/receiving module 301b is an example of a second communication section provided at the second port and communicating with the second transmitting unit when the second transmitting unit is mounted on the second port. In the present embodiment, the controller 310 allows inheritance of information of the transmitting unit 120 newly mounted on one charge port of the first and second charge ports to another transmitting unit 120 already mounted on the other charge port to thereby allow smooth replacement of the transmitting unit 120. More specifically, the controller 310 writes data (communication identification information, calibration information, measurement data, and measurement date and time) recorded in the IC tag 221 of the transmitting unit 120 newly mounted on one charge port to the IC tag 221 of another transmitting unit 120 already mounted on the other charge port.

In the controller 310 executing the above-described processing, an acquirer 311 acquires data recorded in the IC tag 221 of the transmitting unit 120 mounted on the charge port by using the IC tag transmitting/receiving module 301a or 301b and stores the acquired data in a buffer 312. The acquirer 311 is an example of data acquiring means for acquiring transmission data, including communication identification information for transmitting bio-information from one of the first and second transmitting units to the external unit, by the communication section in the first port or the second port when the respective first transmitting unit and the second transmitting unit is newly placed on the first/second port. The controller 310 is an example of a device that carries out a program to acquire data. A determiner 313 determines whether or not it is possible to carry out data acquisition by the acquirer 311 and data transmission by a transmitter 314, and also serves as a determining means for determining whether charging of the transmitting units at the respective ports is completed. The controller 310 is once again an example of a device that carries out a program to determine the charging state. The transmitter 314 transmits (writes) the data retained in the buffer 312 to the IC tag 221 of the transmitting unit 120 by using the IC tag transmitting/ receiving module 301a or 301b. The transmitter 314 is an example of transmitting means that transmits the transmission data acquired by the acquirer. The controller 310 is an example of a device to carry out a program to transmit data. The above-described functions of the controller 310 and functions to be explained in more detail below may be realized by dedicated hardware, or part or all thereof may be realized through running of a predetermined program by a CPU included in the controller 310.

4. Method for Using Body Fluid Component Measuring System

Next, a method for using the body fluid component measuring system 100 according to the present embodiment will be described with reference to FIG. 5. To simplify the following explanation, the blood glucose level will be described as an example of the concentration of a body fluid component calculated in the transmitting unit.

As described above, the body fluid component measuring system 100 according to the present embodiment includes the sensor unit 110, the transmitting unit 120, and the display unit 130. Among them, the transmitting unit 120 is detachably attached to the sensor unit 110 and therefore it is desirable that it has light weight and small size for the subject. On the other hand, the transmitting unit 120 needs to have a sufficient power supply to supply the power necessary for measurement to the sensor unit 110 and provide power for carrying out communication with the display unit 130.

For such circumstances, in the body fluid component measuring system 100 according to the present embodiment, plural transmitting units are prepared and the configuration is so made that the transmitting unit being used and the transmitting unit being charged are alternately replaced and used. For example, two units of a transmitting unit A and a transmitting unit B are prepared as the transmitting units 120. In the state in which the transmitting unit A is attached to the sensor unit 110, the transmitting unit B is charged by the charge device 300. In the state in which the transmitting unit A is being charged by the charge device 300, the transmitting unit B is attached to the sensor unit 110. As described above, two charge ports are prepared in the charge device 300 of the present embodiment. When the transmitting unit A is newly mounted on one charge port for a charge in the state in which the transmitting unit B is being charged at the other port, the charge device 300 operates so that data recorded in the IC tag 221 of the transmitting unit A may be transferred to the IC tag 221 of the transmitting unit B. Similarly, when the transmitting unit B is newly mounted on one charge port for a charge in the state in which the transmitting unit A is being charged at the other port, the charge device 300 operates so that data recorded in the IC tag 221 of the transmitting unit B may be transferred to the IC tag 221 of the transmitting unit A.

Employing such a configuration makes it possible to suppress the capacity (power capacity) of the secondary battery mounted in the transmitting unit A and the transmitting unit B as much as possible (i.e. makes it possible to reduce the size of the secondary battery) and convenience for the subject is also not impaired. Furthermore, continuous monitoring of the blood glucose level is interrupted only at the time of replacement between the transmitting unit A and the transmitting unit B, and it also becomes possible to shorten this interruption time. Furthermore, according to the present embodiment, although the transmitting unit 120 is replaced, there is no need to remake the setting of pairing between the display unit 130 and the transmitting unit 120 because the communication identification information used for wireless communication with the display unit 130 is inherited or transferred. In addition, because the calibration information is inherited or transferred, there is no need to reacquire the calibration information relating to the placed sensor unit 110. Moreover, because measurement data (blood glucose level data) is inherited or transferred, loss of data that has not yet been transmitted to the display unit 130 can be prevented. However, because of a limit on the storage capacity of the IC tag 221, a predetermined number of recent measurement data are retained in the IC tag 221.

Figure 5:
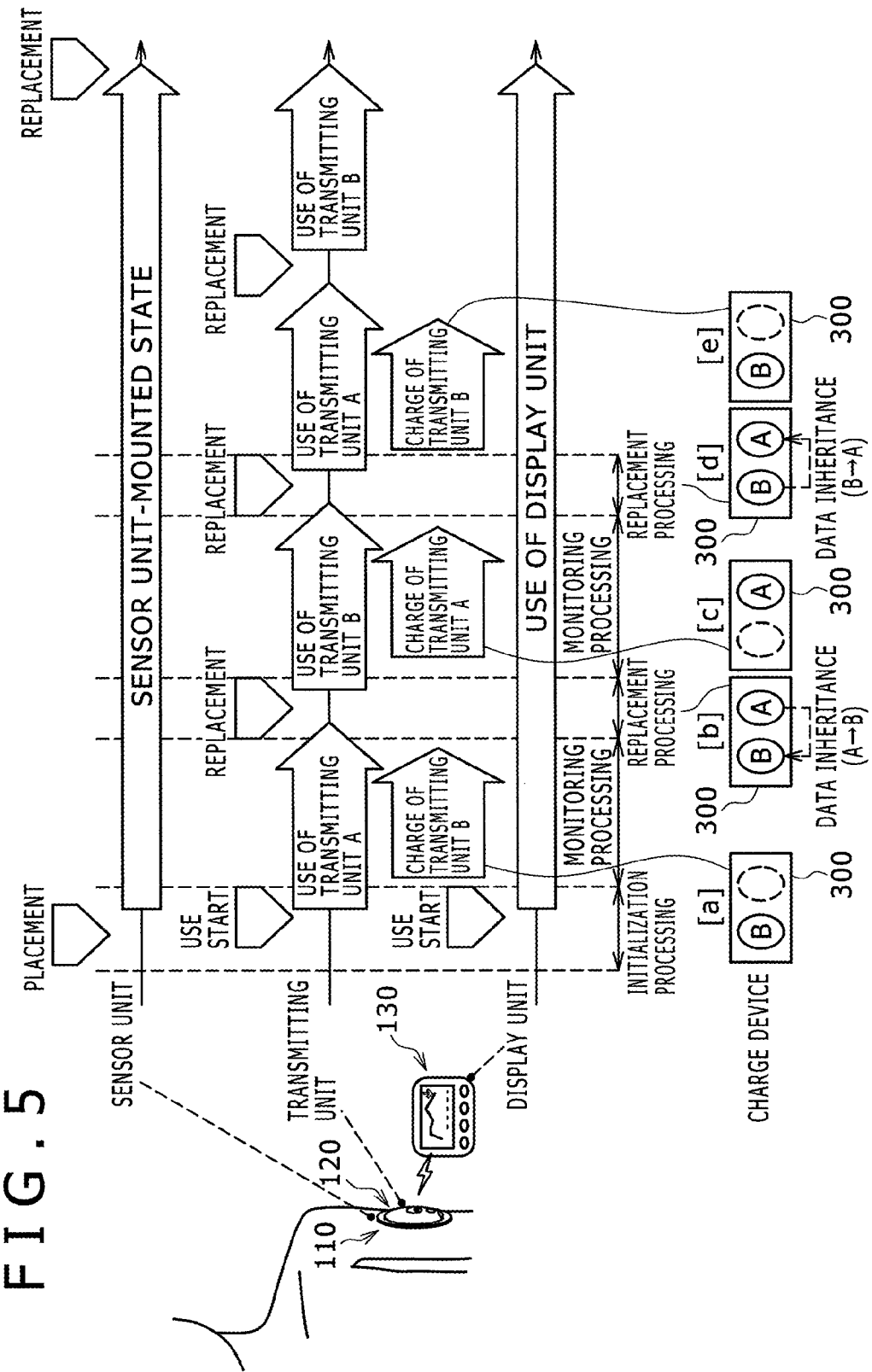
FIG. 5 is a diagram for explaining a method of using the respective units configuring the body fluid component measuring system.

FIG. 5 is a diagram showing an example of a method of using the body fluid component measuring system 100 according to the present embodiment. As shown in FIG. 5, in the body fluid component measuring system 100, three processing states (initial processing state, monitoring processing state, and replacement processing state) exist.

In the initial processing, the sensor unit 110 (sensor unit name: sensor unit A) is placed on the skin of a subject and one transmitting unit 120 (hereinafter, transmitting unit A) is attached to this sensor unit 110. Thereafter, when the power supply is turned on, communication between the transmitting unit A and the display unit 130 is established. Details of the initial processing will be described later.

Upon the establishment of the communication between the transmitting unit A and the display unit 130 in the initial processing, the monitoring processing of the blood glucose level is started in the transmitting unit A. In the monitoring processing, measurement by the sensor unit 110 is carried out based on an order from the CPU 222 based on the program that is stored in the memory 128 in the transmitting unit A and is to calculate the concentration of a body fluid component. Furthermore, blood glucose level data that is calculated based on measurement data and stored in the IC tag 221 is transmitted to the display unit 130 by the transmitting unit A based on an order from the CPU 232 in the display unit 130 to thereby be displayed on the display unit 130. Details of the monitoring processing will also be described later.

While the transmitting unit A is being used, another transmitting unit 120 (hereinafter, transmitting unit B) is charged by the charge device 300 ([a]). At a time when the power of the secondary battery 224 of the transmitting unit A is consumed and the remaining level has become low, the subject replaces the transmitting unit A with the transmitting unit B for which the charge has been completed. Details of the replacement processing will also be described later. Furthermore, in the replacement of the transmitting unit A, the user mounts the transmitting unit A on the charge device 300 before taking out the transmitting unit B from the charge device 300, to make the state in which the two transmitting units 120 (transmitting unit A and transmitting unit B) are simultaneously mounted on the charge device 300 ([b]). In this state, data including communication identification information is inherited or transferred from the transmitting unit A to the transmitting unit B. Thereafter, the transmitting unit B is taken out from the charge device 300 to be mounted on the sensor unit 110 and charging of the secondary battery 224 of the transmitting unit A is performed. The data inheritance processing in the charge device 300 will be described later.

When the transmitting unit B taken out from the charge device 300 is attached to the sensor unit 110 after the replacement processing is completed and communication between the transmitting unit B and the display unit 130 is established, the monitoring processing of the blood glucose level is started in the transmitting unit B. As described above, in the monitoring processing, measurement by the sensor unit 110 is carried out based on an order from the CPU 222 in the transmitting unit B. Furthermore, blood glucose level data that is calculated based on measurement data and stored in the IC tag 221 is transmitted to the display unit 130 by the transmitting unit B based on an order from the CPU 232 in the display unit 130 to thereby be displayed on the display unit 130.

While the monitoring processing by the transmitting unit B is being executed, the transmitting unit A is connected to the charge device 300 to undergo charging ([c]). At a time when the power in the secondary battery 224 of the transmitting unit B is consumed and the remaining level has become low, the subject replaces the transmitting unit B with the transmitting unit A for which the charge has been completed. The state in the charge device 300 at this time is shown in [d] and [e]. Here, data inheritance or transfer from the transmitting unit B to the transmitting unit A is carried out. Thereafter, the transmitting unit A is taken out from the charge device 300 and mounted on the sensor unit 110, and the secondary battery 224 of the transmitting unit B is charged by the charge device 300. From then on, in the period until replacement timing of the sensor unit 110, the monitoring processing is continued with repetition of replacement between the transmitting unit A and the transmitting unit B.

The measurement in the sensor unit 110 is carried out based on an order from the CPU 222 based on the program that is stored in the memory 128 in the transmitting unit 120 and is performed to calculate the concentration of a body fluid component. The blood glucose level data calculated in the transmitting unit 120 based on the measurement data from the sensor unit 110 is stored in the IC tag 221. Therefore, the display unit 130 does not need to be always placed operably near the transmitting unit 120 during the monitoring processing. That is, the monitoring processing is not interrupted even when the power supply of the display unit 130 is set to the off-state. Thus, it is sufficient that the number of display units 130 is one.

Referring once again to the illustration in FIG. 5, when it is time to replace the sensor unit 110, the sensor unit 110 is replaced and the new sensor unit 110 is placed on the skin of the subject. In this case, the display unit 130 and the transmitting unit A/transmitting unit B used so far continue to be used. However, the initial processing is executed again because the sensor unit 110 is replaced.

As described above, in the body fluid component measuring system 100 according to the present embodiment, plural transmitting units 120 are prepared, used and charged in an alternately repeating manner. This makes it possible to realize reduction in the weight and size of the transmitting unit 120 and shortening of the interruption time of the monitoring processing.

5. Functions for Realizing Above-Described Using Method in Body Fluid Component Measuring System Set forth next is a description about the functions of the respective sections for realizing the method of use of the body fluid component measuring system 100 according to the present embodiment as explained above.

As described above with reference to FIG. 5, the transmitting unit 120 is replaced with another transmitting unit 120 every time the remaining power level of the secondary battery 224 becomes low. Therefore, it is inconvenient for the subject that, in the replacement processing, the processing executed in the initial processing (input processing of information necessary for calculation of calibration information, setting processing of information necessary for establishing communication between transmitting unit and display unit, and so forth) is executed again. Furthermore, if a configuration in which blood glucose level data calculated based on measurement data is read out anew again from the replaced transmitting unit is employed, the workload is high for the subject.

In other words, reducing the workload of the subject at the time of the replacement processing makes it possible to further shorten the interruption time of the monitoring processing. For such circumstances, in the body fluid component measuring system 100 according to the present embodiment, the charge device 300 is equipped with the following functions.

To allow calibration information calculated when the sensor unit 110 is placed to be inherited by or transferred to the next transmitting unit 120 in replacement of the transmitting unit 120.

To allow blood glucose level data calculated in the transmitting unit 120 based on a measurement result in the sensor unit 110 to be inherited by or transferred to the next transmitting unit 120 in replacement of the transmitting unit 120.

To allow communication identification information be inherited to the next transmitting unit 120 so that the transmitting unit 120 after replacement can immediately establish communication with the display unit 130 in the case in which the sensor unit 110 is not replaced but only the transmitting unit 120 is replaced.

In the body fluid component measuring system 100 according to the present embodiment, in order to realize the above-described functional attributes in the above-described using method, the configuration is employed in which the IC tag 221 is provided in the transmitting unit 120 and the various kinds of information that should be inherited by or transferred to the next transmitting unit 120 in replacement of the transmitting unit 120 are stored in the IC tag 221. The following will set forth a description about a specific processing flow for realizing the above-described functions in the respective kinds of processing shown in FIG. 5 (initial processing, monitoring processing, replacement processing, and charge processing).

6. Flow of Initial Processing

First, the flow of the initial processing in the body fluid component measuring system 100 according to the present embodiment will be described with reference to the flowchart or process routine shown in FIG. 6 which illustrates the flow of the initial processing of the respective units in the body fluid component measuring system 100 according to the present embodiment.

Figure 6:
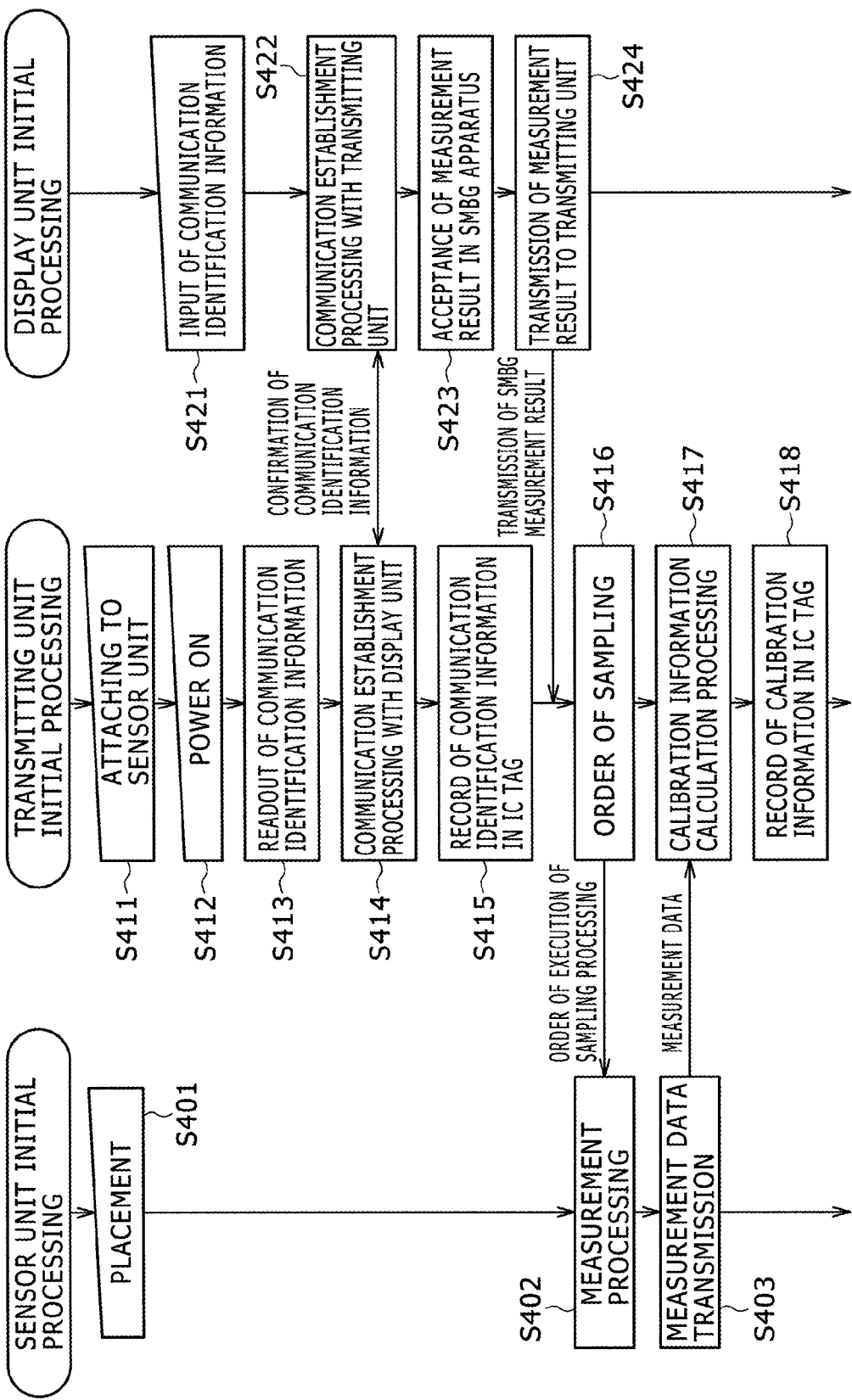
FIG. 6 is an illustration showing flow of an initial process in the body fluid component measuring system.

As shown in FIG. 6, the sensor unit 110 is placed on a subject in a step S401 and the transmitting unit 120 is attached to this sensor unit 110 in a step S411. In a step S421, input of the communication identification information (communication ID) necessary for communication between the transmitting unit 120 and the display unit 130 is made to the display unit 130, for example by the user. In a step S412, the subject turns on the power supply of the transmitting unit 120 to activate the transmitting unit 120.

When the power supply of the transmitting unit 120 is turned on in the step S412, the processing proceeds to a step S413. Communication identification information is not stored in the IC tag 221 of the transmitting unit 120 at the timing of the step S413 as the initial processing. Therefore, the transmitting unit 120 reads out default communication identification information retained in the memory 128. Then, the transmitting unit 120 attempts to establish wireless communication with the display unit 130 by using the read communication identification information (step S414 and step S422). Specifically, the transmitting unit 120 and the display unit 130 mutually confirm the communication identification information and start wireless communication if the pieces of information are identical. On the other hand, they do not perform wireless communication if the pieces of information are not identical. It is also possible that, when communication is not established, an error message indicating the failure in the establishment is output. Communication may be established by displaying a list of the communication identification information of the transmitting unit 120 with which communication can be established in the display unit 130 and making the user select the information (in this case, input operation of communication identification information in S421 is unnecessary). Upon establishing wireless communication with the display unit 130 in this manner, the transmitting unit 120 records the communication identification information used for this wireless communication in the IC tag 221 (step S415). The communication identification information recorded in the IC tag 221 will be inherited by or transferred to another (charge-completed) transmitting unit 120 when this transmitting unit 120 is charged in the charge device 300.

In the display unit 130 for which the communication with the transmitting unit 120 has been established, the processing proceeds to a step S423, where the display unit 130 accepts a measurement result obtained by performing measurement in SMBG apparatus in advance. That is, a user measures blood glucose level with a SMBG device and inputs the measurement result into the display unit 130. In the display unit 130 that has accepted the measurement result obtained by performing measurement in SMBG apparatus in advance, the processing proceeds to a step S424, where the display unit 130 transmits this accepted SMBG measurement result to the transmitting unit 120.

In the transmitting unit 120 that has received the SMBG measurement result from the display unit 130, the processing proceeds to a step S416, where the transmitting unit 120 orders the sensor unit 110 to execute sampling processing for generating calibration information. The sensor unit 110 that has received the order of execution of sampling processing executes measurement processing in a step S402 and transmits measurement data to the transmitting unit 120 in step S403. In the present embodiment, measurement data recorded in the IC tag 117 is read by the IC tag transmitting/receiving module 122 of the transmitting unit 120.

In a step S417, the transmitting unit 120, which has received the measurement data from the sensor unit 110, calculates calibration information from this received measurement data and the SMBG measurement result. Furthermore, the processing proceeds to a step S418, where the transmitting unit 120 records the calculated calibration information in the IC tag 221. Due to this, the calibration information is included in the data to be inherited to another transmitting unit 120 and thus it becomes unnecessary to calculate the calibration information again at the time of replacement of the transmitting unit 120.

7. Flow of Monitoring Processing

Next, the flow of the monitoring processing of the body fluid component measuring system 100 according to the present embodiment will be described with reference to FIG. 7 which is a flowchart showing the flow of the monitoring processing of the body fluid component measuring system 100 according to the present embodiment.

Figure 7:
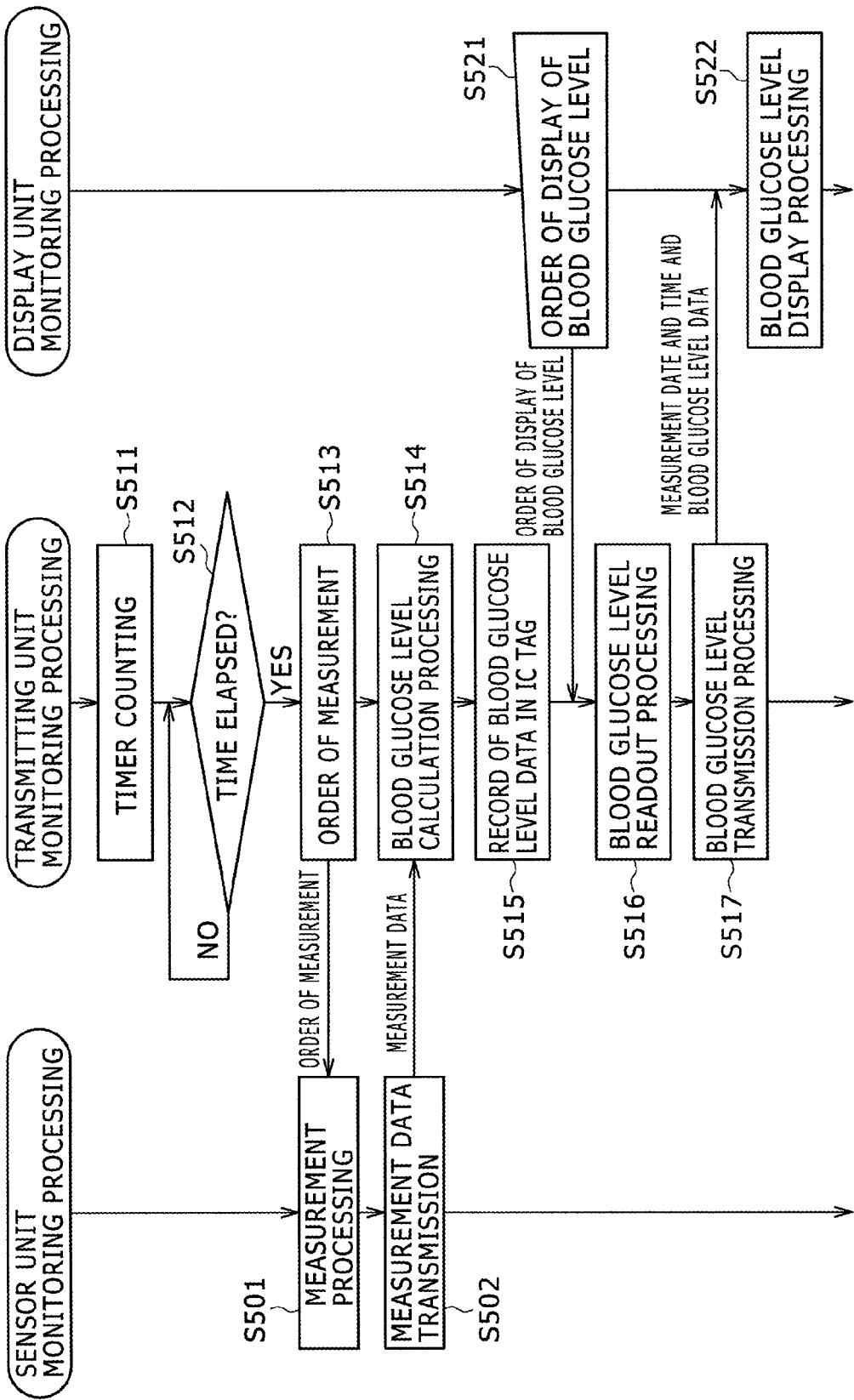
FIG. 7 is an illustration showing flow of monitoring processing in the body fluid component measuring system.

As shown in FIG. 7, timer counting is started in a step S511 and it is determined by the CPU 222 in the transmitting unit 120 whether or not a predetermined time has elapsed in a step S512. If it is determined in step S512 that the predetermined time has elapsed, the processing proceeds to step S513, where the transmitting unit 120 orders the sensor unit 110 to perform measurement. The order of measurement is thus transmitted from the transmitting unit 120 to the sensor unit 110 at a predetermined time interval.

In step S501, the sensor unit 110, which has received the order of measurement from the transmitting unit 120, executes measurement processing. Moreover, in step S502, the sensor unit 110 transmits measurement data obtained as the result of the measurement processing to the transmitting unit 120. In the present embodiment, the measurement data recorded in the IC tag 117 is read by the IC tag transmitting/receiving module 122 of the transmitting unit 120. In step S514, the transmitting unit 120, which has received the measurement data from the sensor unit 110, calculates blood glucose level data based on this received measurement data and the calibration information stored in the IC tag 221. Furthermore, in a step S515, the transmitting unit 120 records the calculated blood glucose level data in the IC tag 221 in association with the present date and time (measurement date and time). The measurement data recorded in the IC tag 221 is measurement data corresponding to a predetermined number of times determined depending on the memory capacity of the IC tag 221. The CPU 222 controls the recording of the measurement data in the IC tag 221 so that the latest measurement data corresponding to a predetermined number of times is retained.

In the above-described manner, the communication identification information and the calibration information obtained in the initial processing are recorded in the IC tag 221 and the data recorded in the IC tag 221 is inherited by or transferred to another transmitting unit in the charge device 300. Due to this, even when the transmitting unit 120 is replaced, the communication identification information and the calibration information used for wireless communication and calculation processing of the blood glucose level in the transmitting unit 120 before the replacement can be inherited or transferred as they are. Furthermore, because the measurement date and time and the measurement data are recorded in the IC tag 221, loss due to the replacement of the transmitting unit 120 can be prevented also about the measurement data that has not yet been transmitted to the display unit 130.

In a step S521, upon accepting an order of display of a blood glucose level from the subject, the display unit 130 transmits this order of display of a blood glucose level to the transmitting unit 120. In a step S516, the transmitting unit 120, which has received the order of display of a blood glucose level, reads out the blood glucose level that has not yet been transmitted to the display unit 130 and its measurement date and time from the IC tag 221.

In a step S517, the blood glucose level data and the measurement date are transmitted to the display unit 130 by the transmitting unit 120. The blood glucose level data and the measurement date and time transmitted by the transmitting unit 120 are displayed on the display unit 130 in a step S522.

8. Flow of Replacement Processing

The flow of the replacement processing of the body fluid component measuring system 100 according to the present embodiment will next be described with reference to FIG. 8 which illustrates the flow of the replacement processing of the body fluid component measuring system 100 according to the present embodiment.

Figure 8:
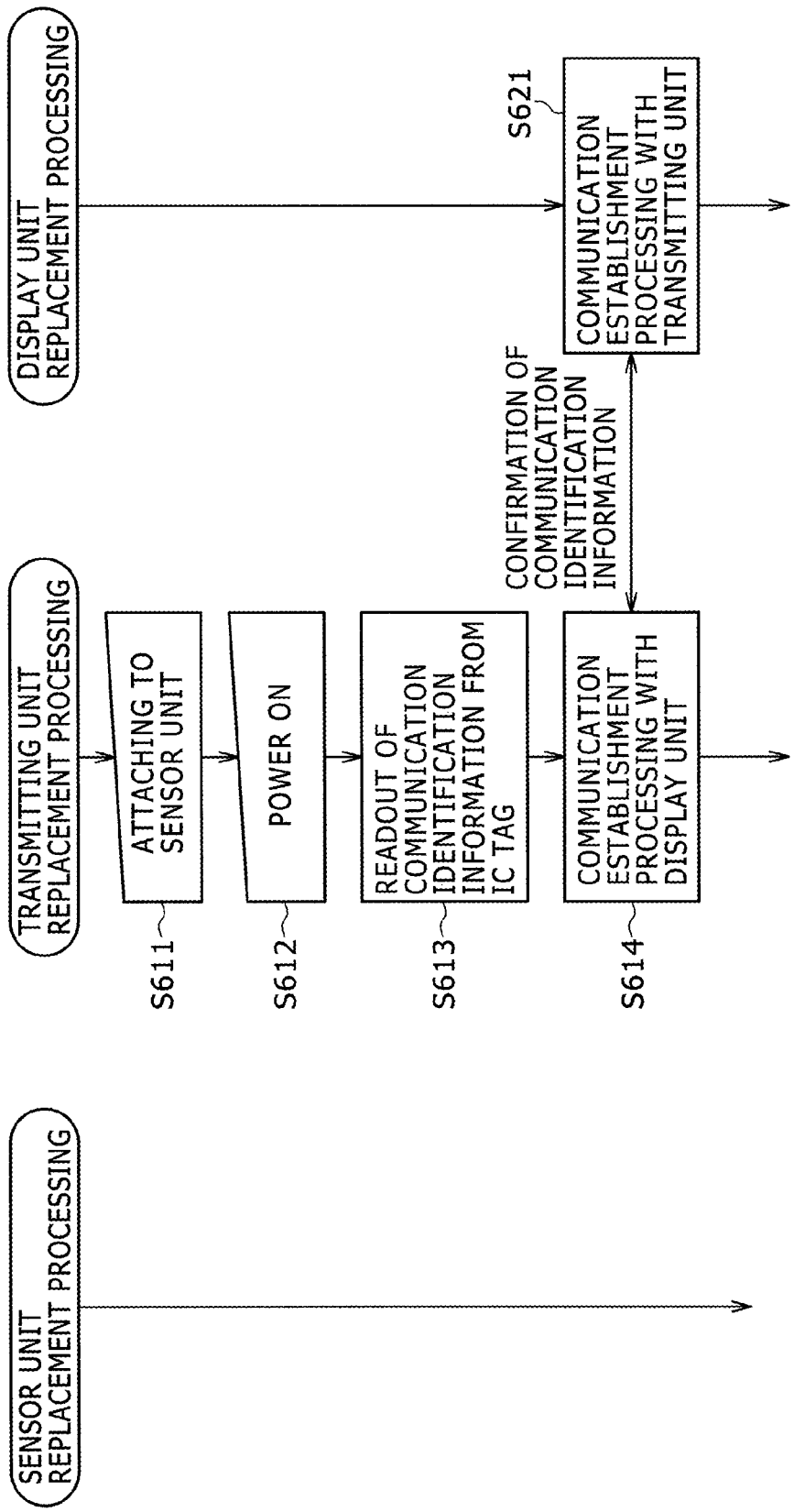
FIG. 8 is an illustration showing flow of replacement processing in the body fluid component measuring system.

As shown in FIG. 8, in step S611, the new transmitting unit 120 is attached to the sensor unit 110. In step S612, the power supply of this new transmitting unit 120 is turned on by the subject and the transmitting unit 120 is activated. Thereupon, the processing proceeds to step S613. In step S613, the transmitting unit 120 reads out the communication identification information stored in the IC tag 221. In steps S614 and S621, the transmitting unit 120 attempts to establish wireless communication with the display unit 130 by using this communication identification information. If the communication identification information is not recorded in the IC tag 221 at this time, the transmitting unit 120 executes the initial processing described above with FIG. 6. The display unit 130 compares the communication identification information used when communication is performed with the transmitting unit 120 before replacement with the communication identification information read from the sensor unit 110 by the transmitting unit 120 after the replacement, and establishes wireless communication if they are identical. On the other hand, wireless communication is not established if they are not identical.

As described later with reference to FIG. 9, data of the IC tag 221 is written to the IC tag 221 of another transmitting unit 120 in the charge device 300. Therefore, due to recording of the communication identification information between the transmitting unit 120 and the display unit 130 in the IC tag 221, the communication identification information is inherited by or transferred even when the transmitting unit 120 is replaced. This can reduce the workload of the subject at the time of the replacement of the transmitting unit 120 and allows shortening of the replacement time when the transmitting unit 120 is replaced. That is, the time for which continuous monitoring of the blood glucose level is interrupted can be shortened.

9. Operation of Charge Device 300 (Flow of Transfer Processing)

FIG. 9 is a flowchart for explaining the operation of the charge device 300. The description which follows will describe a situation in which the transmitting unit 120 is newly mounted on the first charge port 300a for purposes of charging. Operation when the transmitting unit 120 is newly mounted on the second charge port 300b is processing in which the first and second charge ports are translated to the second and first charge ports, respectively, in the operation to be described below. The respective steps in the following are realized mainly through running of a program, stored in a memory in the diagram, by the controller 310.

In step S801, the determiner 313 of the charge device 300 determines whether or not the transmitting unit 120 is newly mounted in the first and second charge ports. Here, based on switching of the charge port in the vacant state to the mounted state, it is determined that the transmitting unit 120 is mounted. The mounted state can be detected by monitoring the operating states of the power supply sections 302a and 302b for example. The present processing is ended if new mounting of the transmitting unit 120 is not detected. When new mounting of the transmitting unit 120 to the first charge port 300a is detected, the processing proceeds to a step S802. In step S802, the acquirer 311 acquires transmission data from the IC tag 221 of the transmitting unit 120 by using the IC tag transmitting/receiving module 301a of the first charge port 300a, on which the transmitting unit 120 is newly mounted, and retains it in the buffer 312. As described above, in the acquired data, e.g. communication identification information, calibration information, blood glucose level data, measurement date and time, and so forth are included.

Next, in step S803, the determiner 313 determines whether or not another transmitting unit 120 has been already mounted on the second charge port 300b, which is the charge port that is not one on which the transmitting unit 120 is newly mounted. If the second charge port is in the vacant state, the present processing is ended. If another transmitting unit 120 is mounted on the second charge port, the processing proceeds to a step S804. In step S804, the transmitter 314 transmits (writes) the data retained in the buffer 312 in the step S802 to the IC tag 221 of the transmitting unit 120 mounted on the second charge port by using the IC tag transmitting/receiving module 301*b*. Then, in step S805, the controller 310 lights the lamp 322*b* in the second charge port to inform the completion of the data inheritance or transfer. The user can recognize that the data inheritance or transfer has been completed by confirming this lamp lighting, and can surely carry out the data inheritance by taking out the transmitting unit 120 from the charge port after the lamp lighting.

By operating in the above-described manner, the charge device 300 causes data of the transmitting unit 120 newly mounted on one charge port to be inherited to the transmitting unit 120 already mounted on the other charge port. In the charge device 300, the initialization switches 321*a* and 321*b* are provided for the respective charge ports. The controller 310 clears the recording content of the IC tag 221 of the transmitting unit 120 mounted on the charge port in which this initialization switch 321*a* or 321*b* is operated. When the transmitting unit 120 in which the content of the IC tag 221 is cleared in this manner is mounted on the sensor unit 110, the above-described initial processing is executed.

In the above description, it is checked whether or not another transmitting unit is mounted on the other charge port (S803) after data is acquired from the newly mounted transmitting unit 120. However, the processing is not limited in this regard. The processing of steps S802 and S804 may be executed if it is confirmed that the transmitting unit 120 is newly mounted on one charge port and another transmitting unit 120 has been already mounted on the other charge port. That is, it is sufficient that data inheritance or transfer is carried out with employment of, as the execution condition of the data inheritance or transfer, another transmitting unit 120 serving as the transmission destination of the data that should be inherited or transferred when the new transmitting unit 120 is mounted on the other charge port, and the order of check of the respective conditions and so forth is arbitrary.

Furthermore, the execution condition used by the determiner 313 is not limited to the above-described execution condition. For example, that the charge state of the transmitting unit 120 as the data inheritance/transfer target is the charge-completed state may be added to the execution condition. Moreover, if time information such as measurement date and time is present in the data to be inherited or transferred, that this latest time information is newer than the latest time information recorded in the transmitting unit 120 as the data inheritance/transfer target may be added to the execution condition.

Furthermore, in the above-described configuration, data of the newly mounted transmitting unit 120 is inherited by or transferred to the already mounted transmitting unit 120 so that the two transmitting units have the same data. However, the configuration is not limited in this way. For example, after the end of data inheritance/transfer, the data of the IC tag 221 of the newly mounted transmitting unit 120 may be deleted. Alternatively, data may be exchanged between the newly mounted transmitting unit 120 and the already mounted transmitting unit 120.

As is apparent from the above description, in the body fluid component measuring system according to the present embodiment, the configuration in which the capacity of the secondary battery mounted in the transmitting unit 120 is suppressed or reduced as much as possible is employed in order to reduce the weight and size of the transmitting unit 120 and enhance convenience for the subject or user. Due to this reduction in the capacity of the secondary battery, the frequency of interruption about continuous monitoring of the blood glucose level increases. However, according to the present embodiment, the configuration in which the plural transmitting units 120 are prepared, use and charge are alternately repeated is employed. Thus, increase in the cumulative total value of the interruption time can be suppressed.

Moreover, in order to reduce the lowering of convenience accompanying replacement of the transmitting unit and the workload at the time of the replacement, the configuration is employed in which the various kinds of information that should be inherited/transferred in association with replacement of the transmitting unit 120 are inherited/transferred to the transmitting unit 120 as the replacement in the charge device 300. For example, if calibration information is included in the information to be inherited/transferred, calibration information set when the sensor unit 110 is placed is inherited/transferred even when the transmitting unit 120 is replaced. This eliminates the need to input the necessary information again in order to calculate the calibration information again at the time of replacement of the transmitting unit.

Furthermore, if blood glucose level data is included in the information to be inherited/transferred, blood glucose level data calculated in the transmitting unit 120 before replacement is inherited/transferred even when the transmitting unit 120 is replaced. This makes it possible to, even after the replacement, make the display unit 130 read out and display the blood glucose level data before the replacement by operation similar to that before the replacement.

Moreover, if communication identification information is included in the information to be inherited/transferred, communication identification information between the transmitting unit 120 and the display unit 130 is inherited/transferred even when the transmitting unit 120 is replaced. This eliminates the need to set the communication identification information again at the time of replacement of the transmitting unit 120.

That is, it becomes possible to shorten the interruption time of monitoring of the blood glucose level, accompanying replacement of the transmitting unit 120, without impairing convenience for the subject. The information to be inherited or transferred may include one other than the above-described information and may be one of the above-described pieces of information.

The communication system between the transmitting unit 120 and the display unit 130 in the above-described embodiment can be a system based on electromagnetic waves. However, the communication system is not limited in this regards, as other communication systems can employed. For example, it is possible to use various known communication systems such as a system using electromagnetic induction, human body communication, and proximity or neighborhood contactless communication.

Furthermore, the above-described embodiment is configured such that the sensor unit 110 and the transmitting unit 120 perform proximity communication by using the IC tag. But the configuration is not limited in this way, and a configuration in which a contact point of a metal or the like is used to electrically connect the transmitting unit and the sensor unit may be employed.

The above-described embodiment also employs a configuration in which two transmitting units 120 are used. But the system disclosed here by way of example is not limited in this way, and the number of transmitting units 120 may be three or more. In this case, the charge device also has three or more charge ports. When the transmitting unit 120 is newly mounted on the charge port, data recorded in the IC tag 221 of the newly mounted transmitting unit 120 is inherited/transferred to other plural transmitting units 120 mounted on the charge device 300.

Moreover, in the above-described first embodiment, the configuration is employed in which blood glucose level data is transmitted from the transmitting unit 120 to the display unit 130 only when an order of display of a blood glucose level from the display unit 130 is present. However, the system is not limited to this arrangement. Transmission to the display unit 130 may be carried out in parallel with writing to the IC tag 221 every time blood glucose level data is calculated in the transmitting unit 120.

Furthermore, plural pairs of charge ports that carry out data inheritance or transfer may exist. This allows plural users to share one charge device 300. In addition, although the configuration in which the transmitting unit 120 is connected to the charge connector is employed for the charge mechanism in the charge port, a configuration to charge it in a contactless manner may also be used. Moreover, although the charge device 300 acquires data recorded in the IC tag by proximity wireless communication in order to acquire the data from the transmitting unit 120, the configuration is not limited thereto. A signal line may be included in the charge connector and the charge device 300 may acquire data from the transmitting unit 120 by the wired measure.

In the above-described embodiment, the charge device 300 having the function to charge the transmitting unit 120 is shown as a device on which the plural transmitting units 120 are placed to transfer data. However, the device is not limited in this way. For example, it is obvious that a data transfer device intended only to transfer data, i.e. one obtained by omitting the charge function from the above-described charge device 300, may be employed. In addition, although wireless communication is employed as communication between the transmitting unit 120 and the display unit 130, which is an external device, the configuration is not limited to this configuration and the communication may be wired communication.

The detailed description above describes embodiments of a data transfer device, data transfer system and data transfer method representing one example of the data transfer device, data transfer system and data transfer method disclosed here. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A data transfer device which receives respective transmitting units that are individually detachably attachable to a sensor unit configured to be at least partially placed in a living body of a subject to acquire a biosignal of the subject and to acquire bio-information from the biosignal acquired in the sensor unit to transmit the bio-information to an external unit, the data transfer device comprising:
a first port configured to receive a first transmitting unit and a second port configured to receive a second transmitting unit;
a first communication section provided at the first port and configured to communicate with the first transmitting unit when the first transmitting unit is mounted on the first port, and a second communication section provided at the second port and configured to communicate with the second transmitting unit when the second transmitting unit is mounted on the second port;
data acquiring means for acquiring transmission data, including communication identification information for transmitting the bio-information from one of the first and second transmitting units to the external unit, by the communication section provided in one of the first port and the second port when the respective first transmitting unit and the second transmitting unit is newly placed on the one of the first port and the second port; and
transmitting means configured to transmit to the transmission data acquired by the data acquiring means to the other of the first and second transmitting units.

2. The data transfer device according to claim 1, wherein the first and second ports are charge ports which charge the first and second transmitting units respectively.

3. The data transfer device according to claim 1, wherein the first communication section and the second communication section are each a reader/writer of an IC tag.

4. The data transfer device according to claim 1, wherein the transmission data acquired by the data acquiring means includes calibration information used when the bio-information is calculated from the biosignal acquired from the sensor unit.

5. The data transfer device according to claim 1, wherein the transmission data acquired by the data acquiring means includes bio-information that has not yet been transmitted to the external unit by the one of the first and second transmitting units.

6. The data transfer device according to claim 5, wherein the transmission data acquired by the data acquiring means includes a predetermined number of pieces of a bio-information recently acquired by the one of the first and second transmitting units and measurement date and time of the bio-information.

7. The data transfer device according to claim 1, further comprising:
determining means for determining whether charging of the first transmitting unit at the first port is completed and for determining whether charging of the second transmitting unit at the second port is completed; and
the transmitting means transmits the transmission data when the determining means determines that charging of the other of the first and second transmitting units is completed.

8. The data transfer device according to claim 1, wherein the transmission data acquired by the data acquiring means includes measurement date and time of the bio-information, and wherein the transmitting means transmits the transmission data when the measurement date and time included in the transmission data acquired from the one of the first and second transmitting units which is newly mounted is newer than the measurement date and time included in data acquired from the other of the first and second transmitting units.

9. A data transfer system comprising:
at least two transmitting units each separately detachably attachable to a sensor unit which is configured to be at least partially placed in a living body of a subject to acquire a biosignal of the subject, one of the transmitting units being configured to acquire bio-information from the biosignal acquired in the sensor unit to transmit the bio-information to an external unit, the at least two transmitting units comprising one transmitting unit and an other transmitting unit;

the external unit that receives the bio-information transmitted from one of the transmitting units; and a data transfer device, the data transfer device comprising:
first and second ports at which respective ones of the transmitting units are to be individually placed;
a first communication section provided at the first port and with one of the transmitting units placed at the first port, and a second communication section provided at the second port and with an other of the transmitting units placed at the second port;
data acquiring means for acquiring transmission data including communication identification information for transmitting to the external device the bio-information from the transmitting unit placed at either one of the first and second ports when the transmitting unit is newly placed at the one port; and
transmitting means for transmitting the transmission data acquired by the data acquiring means to the transmitting unit placed at the other of the first and second ports by using the communication section provided in the other of the first and second ports when another of the transmitting units is placed at the other of the first and second ports.

10. The data transfer system according to claim 9, wherein the data transfer device further comprises a buffer which stores the transmission data acquired by the acquiring means.

11. The data transfer device according to claim 9, wherein the first and second ports are charge ports which charge the transmitting units placed at the first and second ports.

12. The data transfer device according to claim 9, wherein the first communication section and the second communication section are each a reader/writer of an IC tag.

13. A method of transferring data from one transmitting unit placed at a first port of a transfer device, the one transmitting unit being detachably attachable to a sensor unit configured to be at least partially placed in a living body of a subject to acquire a biosignal of the subject, the one transmitting unit acquiring bio-information based on the biosignal acquired in the sensor unit to transmit the bio-information to an external unit, the transfer device including a second port different from the first port, the method comprising:
placing an other transmitting unit different from the one transmitting unit at the second port of the transfer device, the other transmitting unit possessing transmission data including communication identification information for transmitting the bio-information;
the transfer device acquiring the transmission data, including the communication identification information for transmitting the bio-information, from the other transmitting unit; and
the transfer device transmitting, to the one transmitting unit placed at the first port of the transfer device, the transmission data, including the communication identification information for transmitting the bio-information, acquired from the other transmitting unit.

14. The method according to claim 13, further comprising charging the transmitting unit placed at the first port of the transfer device.

15. The method according to claim 13, further comprising storing the transmission data, including the communication identification information for transmitting the bio-information, acquired from the other transmitting unit.

16. The method according to claim 13, wherein the transmission data is acquired by way of a reader/writer of an IC tag.

17. The method according to claim 13, further comprising charging the transmitting unit placed at the first port of the transfer device, determining whether charging of the first transmitting unit placed at the first port is completed, and transmitting the transmission data to the one transmitting unit placed at the first port when it is the determined that full charging of the transmitting unit placed at the first port is completed.

* * * * *